US009453922B2

(12) United States Patent
Stodilka et al.

(10) Patent No.: US 9,453,922 B2
(45) Date of Patent: Sep. 27, 2016

(54) SYSTEM AND METHOD FOR CORRECTING ATTENUATION IN HYBRID MEDICAL IMAGING

(75) Inventors: Robert Z. Stodilka, London (CA); Jean Theberge, London (CA); Benoit Lewden, London (CA); Frank S. Prato, London (CA); R. Terry Thompson, London (CA)

(73) Assignee: Multi-Magnetics Incorporated, London (CA)

( * ) Notice: Subject to any disclaimer, the term of this patent is extended or adjusted under 35 U.S.C. 154(b) by 0 days.

(21) Appl. No.: 12/556,358

(22) Filed: Sep. 9, 2009

(65) Prior Publication Data

US 2010/0204563 A1 Aug. 12, 2010

Related U.S. Application Data

(60) Provisional application No. 61/095,382, filed on Sep. 9, 2008.

(51) Int. Cl.
| | |
|---|---|
| *A61B 5/00* | (2006.01) |
| *G01T 1/16* | (2006.01) |
| *A61B 5/055* | (2006.01) |
| *A61B 6/03* | (2006.01) |
| *G01R 33/48* | (2006.01) |
| *G01T 1/164* | (2006.01) |

(52) U.S. Cl.
CPC ........... *G01T 1/1603* (2013.01); *A61B 5/0035* (2013.01); *A61B 5/055* (2013.01); *A61B 6/037* (2013.01); *G01R 33/481* (2013.01); *G01T 1/1647* (2013.01); *A61B 2090/374* (2016.02)

(58) Field of Classification Search
CPC ... G01T 1/1603; G01T 1/1647; A61B 6/037; A61B 5/055; A61B 5/0035; A61B 2090/374; G01R 33/481
USPC ......................... 600/410, 411, 436; 324/318; 250/363.04
See application file for complete search history.

(56) References Cited

U.S. PATENT DOCUMENTS

| | | | |
|---|---|---|---|
| 6,430,430 B1 | 8/2002 | Gosche | |
| 8,600,136 B2 * | 12/2013 | Schweizer | ........... G01R 33/481 382/131 |
| 2016/0071263 A1 * | 3/2016 | Thiruvenkadam | .... G06T 7/0083 382/131 |

FOREIGN PATENT DOCUMENTS

| | | |
|---|---|---|
| WO | 2004/042546 | 5/2005 |
| WO | 2008/064319 | 5/2008 |

OTHER PUBLICATIONS

Zaidi et al. Magnetic resonance imaging-guided attenuation and scatter corrections in three-dimensional brain positron emission tomography. Med. Phys. 30 (5), May 2003 pp. 937-948.*

(Continued)

*Primary Examiner* — Amanda Lauritzen Moher
(74) *Attorney, Agent, or Firm* — Ridout & Maybee LLP

(57) ABSTRACT

A hybrid medical imaging system comprises a nuclear medicine imaging subsystem for capturing an image of a target region of a subject, a magnetic resonance imaging (MRI) subsystem for capturing an MRI image of the target region based on at least one MRI parameter and processing structure communicating with the subsystems. The processing structure processes the MRI image to estimate attenuation within the target region and uses the estimated attenuation to correct the image captured by the nuclear medicine imaging subsystem.

25 Claims, 7 Drawing Sheets

(56) References Cited

OTHER PUBLICATIONS

Ay et al. Computed Tomography Based Attenuation Correction in PET/CT: Principles, Instrumentation, Protocols, Artifacts and Future Trends. Iran J Nucl Med 2007 15 (2) pp. 1-29.*
European Search Report dated Nov. 3, 2011 in corresponding European Application No. 09 01 1552.
Robert Z. Stodilka et al., "Scatter and Attenuation Correction for Brain SPECT Using Attenuation Distributions Inferred from a Head Atlas", Journal of Nuclear Medicine 2000.
K.S. St. Lawrence et al., "Effects of the Apparent Transverse Relaxation Time on Cerebral Blood Flow Measurements Obtained by Arterial Spin Labeling", Magnetic Resonance in Medicine, 2005.
Habib Zaidi, "Is MR-guided Attenuation Correction a Viable Option for Dual-Modality PET/MR Imaging?", Radiology, vol. 244, No. 3, Sep. 2007.
Robert Z. Stodilka et al., "Importance of Bone Attenuation in Brain SPECT Quantification", The Journal of Nuclear Medicine, vol. 39, No. 1, Jan. 1998.
Radiological Society of North America, "Scientific Assembly and Annual Meeting Program", Nov. 25-30, 2007.
Habib Zaidi et al., "Magnetic Resonance Imaging-guided Attenuation and Scatter Corrections in Three-Dimensional Brain Positron Emission Tomography", Med. Phys. 30, May 2003.
Alan Wee-Chung Liew et al., "An Adaptive Spatial Fuzzy Clustering Algorithm for 3-D MR Image Segmentation", IEEE, 2003.
Niels A. Lassen, "A Reappraisal of the Relative Merits of SPET and PET in the Quantitation of Neuroreceptors: the Advantage of a Longer Half-life!", European Journal of Nuclear Medicine, Jan. 1996.
Takashi Koyama et al., "Current Status of Body MR Imaging: Fast MR Imaging and Diffusion-weighted Imaging", The Japan Society of Clinical Oncology, 2006.
Kathrin Kalki et al., "Myocardial Perfusion Imaging with a Combined X-Ray CT and SPECT System", Journal of Nuclear Medicine, 1997.
J. Hong et al., "Magnetic Resonance Imaging Measurements of Bone Density and Cross-Sectional Geometry", Calcified Tissue International, 2000.
Joel S. Karp, et al., "Singles Transmission in Volume-imaging PET with a 137 Cs Source", Phys. Med. Biol. 40, 1995.
Michael Jerosch-Herold et al., "Myocardial Blood Flow Quantification with MRI by Model-independent Deconvolution", Med. Phys. 29, May 2002.
Renjie He, et al., "Implementation of High-Dimensional Feature Map for Segmentation of MR Images", Biomedical Engineering Society, 2005.
J.A. Hartigan et al., "A K-Means Clustering Algorithm", Journal of the Royal Statistical Society, Series C (Applied Statistics), vol. 28 No. 1, 1979.
J. Du et al., "Ultrashort TE Spectroscopic Imaging (UTESI) of the Short T2 Tissues in the Musculoskeletal System", Proc. Intl. Soc. Mag. Reson. Med. 16 (2008).
Z.H. Cho, et al., "Foundations of Medical Imaging", Published by John Wiley & Sons, Inc., copyright 1993.
William B. Handler et al., "Simulation of Scattering and Attenuation of 511 keV Photons in a Combined PET/Field-Cycled MRI System", Physics in Medicine and Biology, 2006.
John Conklin et al., "High-Contrast 3D Neonatal Brain Imaging with Combined T1- and T2-Weighted MP-RAGE", Magnetic Resonance in Medicine, 2008.
Anion F. Chatziioannou, "Instrumentation for Molecular Imaging in Preclinical Research", Proc Am Thorac Soc, vol. 2, 2005.
A.A.O. Carneiro et al., "MRI Relaxometry: Methods and Applications", Brazilian Journal of Physics, vol. 36, No. 1A, Mar. 2006.
Thomas Beyer et al., "A Combined PET/CT Scanner for Clinical Oncology", Journal of Nuclear Medicine, 2000.
Pierrick Bourgeat et al., "MR Image Segmentation of the Knee Bone Using Phase Information", Medical Imaging Analysis II, 2007.
Peter J. Basser et al., "In Vivo Fiber Tractography Using DT-MRI Data", Magnetic Resonance in Medicine, 2000.
Habib Zaidi et al., "Strategies for Attenuation Compensation in Neurological PET Studies", NeuroImage, 2007.
Belma Dogdas et al.; Segmentation of Skull and Scalp in 3-D Human MRI Using Mathematica; Morphology; Signal and Image Processing Institute of Southern California, Los Angeles, California; Laboratory of Neuro Imaging, Department of Neurology, David Geffen School of Medicine at UCLA, Los Angeles, California; 2005 Wiley-Liss, Inc.
Georges El Fakhri et al.; MRI-Guided Spect Perfusion Measures and Volumetric MRI in Prodromal Alzheimer Disease; 2003 American Medical Association.
Matthias Hofmann et al.; MRI-Based Attenuation Correction for PET/MRI: A Novel Approach Combining Pattern Recognition and Atlas Registration; Copyright 2008 by the Society of Nuclear Medicine, Inc.
Habib Zaidi et al.; Strategies for attenuation compensation in neurological PET studies; NeuroImage; www.elsevier.com/locate/ynimg; NeuroImage 34 (2007) 518-541.
Harry R. Marshall et al.; Variable Lung Density Consideration in Attenuation Correction of Whole-Body PET/MRI; The Journal of Nuclear Medicine; Published online: May 7, 2012.
Elena Rota Kops et al.; Alternative Methods for Attenuation Correction for PET Images in MR-PET Scanners; 2007 IEEE Nuclear Science Symposium Conference Record.

* cited by examiner

LOOKUP TABLE OF
KNOWN TISSUE
ATTENUATION
COEFFICIENTS
62

| TISSUE | μ |
|---|---|
| MUSCLE | 0.10 |
| LIVER | 0.09 |
| LUNG 1 | 0.06 |
| LUNG 2 | 0.05 |
| ETC... | |

IN SITU MEASUREMENTS
(FOR EXAMPLE MAGNETIC RESONANCE
SPECTROSCOPY OF BONE DENSITY)
64

COMBINE
INFORMATION

ATTENUATION COEFFICIENT IMAGE
60

T1 WEIGHTED

T2 WEIGHTED

PROTON DENSITY

X-RAY CT 511 keV

PET

FIGURE 8A A. (CT-DERIVED)

FIGURE 8B B. (MRI-DERIVED)

FIGURE 8C C. (LINE-INTEGRAL CORRELATION)

| AXIAL SLICE | MRI PARAMETERS | LINE OF BEST FIT | R² |
|---|---|---|---|
| THORACIC | PDw | Y=0.74X+0.58 | 0.58 |
| THORACIC | T1w+PDw+WSPD1w | Y=0.83X+0.54 | 0.77 |
| ABDOMINAL | T1w+PDw+WSPD1w | Y=0.95X+0.27 | 0.94 |

SYSTEM AND METHOD FOR CORRECTING ATTENUATION IN HYBRID MEDICAL IMAGING

CROSS-REFERENCE TO RELATED APPLICATIONS

This application claims the benefit of U.S. Provisional Application No. 61/095,382 filed on Sep. 9, 2008 entitled "System And Method For Correcting Attenuation In Hybrid Medical Imaging", the content of which is incorporated hereby reference.

FIELD OF THE INVENTION

The present invention relates generally to medical imaging and in particular, to a system and method for attenuation correction in hybrid MRI medical imaging.

BACKGROUND OF THE INVENTION

Hybrid imaging technologies of nuclear medicine imaging and computer tomography such as Positron Emission Tomography/X-ray Computed Tomography (PET/CT) and more recently Single Photon Emission Computed Tomography/CT (SPECT/CT) are well-known. PET/Medical Resonance Imaging (PET/MRI), however, offers several important advantages over PET/CT. Unlike PET/CT where imaging is sequential, PET/MRI enables true simultaneous multi-modality measurement (although there are PET/MRI solutions utilizing field-cycled MRI offering temporally-interleaved PET and MRI). Compared with CT imaging, the technology of magnetic resonance imaging offers much larger breadth in measurement parameters. The well-established measurements of longitudinal and transverse magnetization relaxation (R1, R2) and proton density offer superior soft tissue contrast compared with CT.

Although MRI has difficulties imaging bones due to lack of water content, the marrow can be seen and the bones easily inferred. In MRI, pulse sequences allow for functional imaging (fMRI). In the brain the functional imaging encompasses the detection of blood oxygenation level dependent (BOLD) tissue changes as described in "Intrinsic signal changes accompanying sensory stimulation: functional brain mapping with magnetic resonance imaging" authored by Ogawa et al. (Proc Natl Acad Sci USA 89 5951-5, 1991) and quantitative measurements of blood flow using arterial spin labeling (ASL) as described in "Effects of the apparent transverse relaxation time on cerebral blood flow measurements obtained by arterial spin labeling" authored by St. Lawrence et al. (Magn Reson Med 53 425-33, 2005). In the heart, the functional imaging encompasses contrast agent bolus tracking and wall motion studies as described in "Myocardial blood flow quantification with MRI by model-independent deconvolution" authored by Jerorsch-Herold M et al. (Med Phys 29 886-897, 2002). Further, MRI can measure water diffusion amplitude ("coefficients") as described in "Current status of body MR imaging: fast MR imaging and diffusion-weighted imaging" authored by Koyama et al. (Int J Clin Oncol 11 278-285, 2006), tensors enabling tractographic imaging as described in "In vivo Fiber Tractography using DT-MRI Data" authored by Basser et al. (Mag Reson Med 44 625-632, 2000), and spectroscopy to measure biochemistry. Another advantage of MRI over CT concerns the ionizing radiation association with the latter (typical dose from helical CT of the chest is about 8 mSv, resulting in a 0.03% increased risk of stochastic induction of fatal cancer). Although a typical PET study results in about a 14 mSv dose, the lack of MRI ionizing radiation is of value in serial and pediatric studies. This is not to say, however, that hybridization of PET with MRI is without challenges.

To date, efforts to hybridize modalities has resulted in popular clinical PET/CT and SPECT/CT platforms. There is substantial overlap between SPECT and PET clinical capabilities, with each modality having advantages and disadvantages. SPECT has the advantage of being able to image multiple isotopes simultaneously. Single photon emitting radioisotopes generally have longer radioactive half-lives than their PET counterparts which has implications for radiopharmaceuticals with slow binding kinetics as described in "A reappraisal of the relative merits of SPET and PET in the quantification of neuroreceptors: the advantages of a longer half-life!" authored by Lassen (Eur J Nucl Med 23 1-4, 1996). On the other hand, clinical PET images have superior resolution and sensitivity compared with clinical SPECT, although research-grade pre-clinical SPECT systems (small field-of-view systems for imaging small animals) can outperform pre-clinical PET systems due to positron range issues as described in "Instrumentation for Molecular Imaging in Preclinical Research: Micro-PET and Micro-SPECT" authored by Chatziioannou (Proc Am Thoracic Soc 2 533-536, 2005).

PET, like SPECT, suffers from the physical phenomena of gamma-ray attenuation and scattering. These emission tomography modalities rely on detection of gamma-rays emitted via decay of a radioisotope (bound to a radiopharmaceutical) that is injected into the subject to be imaged. From their point of isotropic emission, the gamma-rays travel through the subject interacting with the tissues of the subject (specifically, the electrons) along the way. During travel, some gamma-rays are absorbed by tissue or are scattered away from the detectors and hence are lost or "attenuated", or are spatially mis-positioned ("scattered"). The obstacles of attenuation and scatter have received much attention over the past decades. Arguably, these obstacles have been overcome for specific circumstances in SPECT and PET, with increasingly sophisticated techniques offering diminishing returns. Attenuation compromises the quantitative accuracy of PET, and correcting for attenuation is a major area of research. In principal, the effects of attenuation can be corrected if the distribution of attenuation coefficients is known. In the past, this was accomplished by hybridizing PET with X-ray CT, yielding the PET/CT apparatus. This hybridization was convenient because CT measurements are easily related to electron density and hence the distribution of attenuation coefficients could be provided with relative ease. In Hybrid MRI/PET, however, there is significant challenge to deriving the distribution of attenuation coefficients, since MRI measurements using contemporary clinical MRI are not easily related to electron density.

The unification of different imaging modalities into a single Hybrid platform is disclosed in "Myocardial Perfusion Imaging with a Combined X-ray CT and SPECT System" authored by Kalki et al. (J Nucl Med 38 1535-1540, 1997) for SPECT/CT and for Positron Emission Tomography (PET) PET/CT in "A Combined PET/CT Scanner for Clinical Oncology" authored by Beyer et al. (J Nucl Med 41 1369-1379, 2000). In both cases, X-ray CT data guided attenuation correction of the gamma-ray measurements.

U.S. Pat. No. 5,672,877 to Liebig et al. discloses a method of coregistering medical image data of different modalities. In the method, an emission scan of an object is performed using a nuclear medicine imaging system to acquire single-photon emission computed tomography (SPECT) image data. A transmission scan of the object is performed simultaneously with the emission scan using the same nuclear medicine imaging system in order to acquire nuclear medicine transmission image data. The emission scan is performed using a roving zoom window, while the transmission scan is performed using the full field of view of the detectors. By knowing the position of the zoom windows for each detection angle, the nuclear medicine transmission image data can be coregistered with the SPECT emission image data as a result of the simultaneous scans. Image data of a modality other than SPECT, such as x-ray computed tomography (x-ray CT) data, magnetic resonance imaging (MRI) data, or positron emission tomography (PET) data, is also provided, which it is desired to have coregistered with the SPECT emission data. The nuclear medicine transmission image data is therefore coregistered with the image data of the different modality. As a result, the image data of the different modality becomes coregistered with the SPECT image data.

U.S. Pat. No. 7,286,867 to Schlyer et al. discloses a combined PET/MRI scanner including a magnet for producing a magnetic field suitable for magnetic resonance imaging, a radiofrequency (RF) coil disposed within the magnetic field produced by the magnet and a ring tomograph disposed within the magnetic field produced by the magnet. The ring tomograph includes a scintillator layer for outputting at least one photon in response to an annihilation event, a detection array coupled to the scintillator layer for detecting the at least one photon outputted by the scintillator layer and for outputting a detection signal in response to the detected photon and a front-end electronic array coupled to the detection array for receiving the detection signal. The front-end array has a preamplifier and a shaper network for conditioning the detection signal.

U.S. Pat. No. 6,927,406 to Zyromski discloses a multi-modal source for imaging with at least one of a gamma camera, a positron emission tomography (PET) scanner and a single-photon-emission computed tomography (SPECT) scanner, and at least one of a computed tomography (CT) scanner, magnetic resonance imaging (MRI) scanner and optical scanner. The multimodal source has radioactive material permanently incorporated into a matrix of material, at least one of a material that is a target for CT, MRI and optical scanning, and a container which holds the radioactive material and the CT, MRI and/or optical target material. The source can be formed into a variety of different shapes such as points, cylinders, rings, squares, sheets and anthropomorphic shapes. The material that is a target for gamma cameras, PET scanners and SPECT scanners and/or CT, MRI and/or optical scanners can be formed into shapes that mimic biological structures.

U.S. Pat. No. 7,378,660 to Case et al. discloses a computer program, method, and system to facilitate hybrid CT attenuation correction. In one embodiment, the method generally includes acquiring data from a scanner, utilizing an ordered subset expectation maximization-bayesian algorithm to reconstruct the acquired data, and forward projecting the reconstructed data. Such a configuration minimizes the computing resources required for reconstruction and improves attenuation correction accuracy.

U.S. Pat. No. 7,348,564 to Wollenweber et al. discloses a method for correcting emission data from Positron Emission Tomography (PET) or SPECT and includes generating a plurality of computed tomography (CT) image data, selecting a portion of the CT image data, processing the selected CT data to generate a plurality of attenuation correction (CTAC) factors at the appropriate energy of the emission data, weighting the CTAC factors to generate an emission attenuation correction map, wherein the weights are determined based on the axial location and the slice thickness of the CT data and the axial location and the slice thickness of the PET or SPECT data, and utilizing the generated attenuation correction map to generate an attenuation corrected PET image.

U.S. Pat. No. 6,628,983 to Gagnon discloses a nuclear imaging system comprising a transmission radiation source that radiates at a plurality of energy levels within a specified energy range. The energy range is divided into two or more energy subranges. Detectors detect the position or trajectory and energy of transmitted radiation and emitted radiation. A sorter sorts the detected radiation into the appropriate energy subrange. Data for each subrange is stored in a plurality of transmission data memories. Reconstruction processors generate a transmission image representation representative of each energy subrange. A combine processor weights each energy subrange image representation with an assigned weighting factor to provide enhancement of at least one feature when the images are combined to generate weighted image representations. The plurality of transmission images are also combined with equal weighting to generate an image representation used to generate attenuation correction factors for correcting the emission data. A reconstruction processor generates a corrected emission image representation. The emission image can be combined with one of the feature-enhanced structural images using a combiner and displayed, allowing the functional emission image to be located with respect to structural or anatomical features. Also, a feature-enhanced structural image, can be used to register the emission image with an image from another modality, such as a computed tomography (CT) image.

U.S. Pat. No. 5,750,991 to Moyers et al. and U.S. Pat. No. 6,040,580 to Watson et al. disclose a method and apparatus for producing radioactive transmission measurements to form multi-dimensional attenuation correction data with a point source of radiation, such as required in positron emission tomography applications. This involves the passing of the point source proximate the face of a selected each of the tomograph units for the formation of a 3-D image, or a selected portion of the tomograph units for a 2-D image. As such, attenuation data, transmission data, detector performance data, etc., can be obtained. This point source of radiation, in one embodiment, is rapidly circulated through a conduit that passes across each detector face under the influence of a transport fluid in, for example, an oscillatory motion to achieve a selected radiation field whereby calculation of transmission measurements within a body positioned within the tomograph scanner is achieved. When not being circulated, the radiation source is held within a shield. Circulation of the transport fluid, typically a hydraulic fluid, is typically accomplished using a positive displacement pump. Position sensors are used to monitor the movement of the source in the conduit as well as its position within the shield. Disconnect units permit removal of the radiation source, as contained in the shield, from the system without accessing any other portions of the system.

Although the above references discloses various imaging techniques, improvements in hybrid medical imaging systems are desired. It is therefore an object of the present invention at least to provide a novel system and method for attenuation correction in hybrid medical imaging.

SUMMARY OF THE INVENTION

A novel technique is presented for facilitating non-uniform attenuation correction in hybrid medical imaging systems such as for example, PET/MRI or SPECT/MRI imaging systems by estimating the distribution of attenuation directly from MRI parameters. The technique uses one or more MRI parameter measurements, such as longitudinal and transverse magnetization weighted imaging, to estimate the distribution of different tissue types in a subject. Subsequently, known energy-dependent attenuation coefficients are assigned to those tissue types, allowing the creation of a non-uniform attenuation map. This attenuation map is then used to guide the reconstruction of the SPECT or PET projection data resulting in attenuation corrected images.

Accordingly, in one aspect there is provided a hybrid medical imaging system comprising a nuclear medicine imaging subsystem for capturing an image of a target region of a subject; a magnetic resonance imaging (MRI) subsystem for capturing an MRI image of said target region based on at least one MRI parameter; and processing structure communicating with said subsystems, said processing structure processing the MRI image to estimate attenuation within said target region and using the estimated attenuation to correct the image captured by said nuclear medicine imaging subsystem.

According to another aspect there is provided a method for hybrid medical imaging comprising producing an image of a target region of a subject based on a radioactive contrast agent in said subject; measuring at least one magnetic resonance parameter of said target region; and estimating attenuation in said target region using said at least one magnetic resonance parameter; and correcting degradations in said image using the estimated attenuation.

According to yet another aspect there is provided a computer readable machine embodying computer program code for causing processing structure of a hybrid medicine imaging system to estimate attenuation in a target region using at least one magnetic resonance parameter of an MRI image; and correct degradations in a nuclear medicine image using the estimated attenuation.

BRIEF DESCRIPTION OF THE DRAWINGS

Embodiments will now be described more fully with reference to the accompanying drawings in which:

FIGS. 8A to 8D show CT and MRI attenuation maps together with line integral data.

DETAILED DESCRIPTION OF THE EMBODIMENTS

Figure 1:
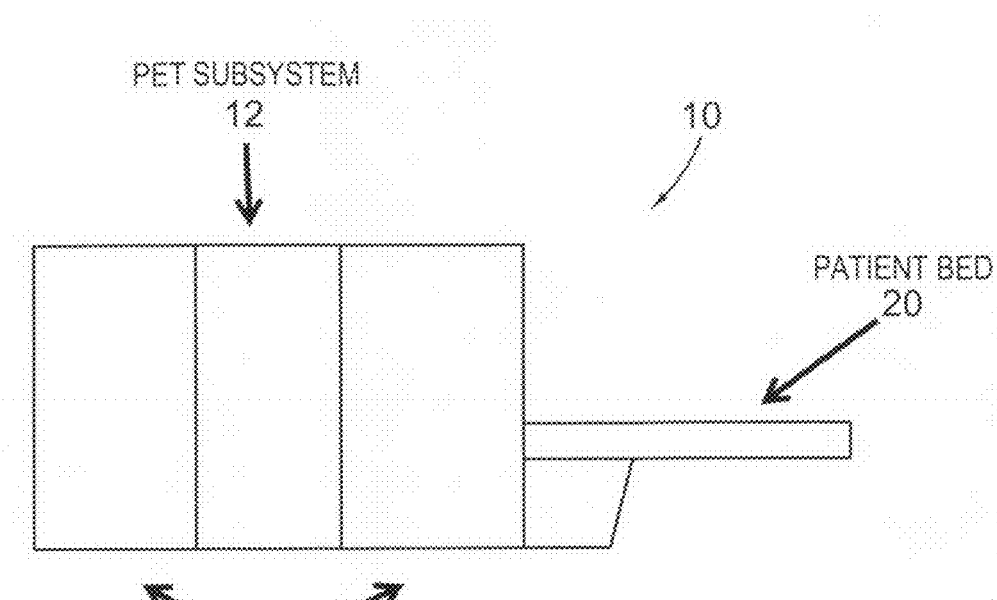
FIG. 1 is a schematic side view of a hybrid magnetic resonance imaging-positron emission tomography system.

Turning now to FIG. 1, a hybrid medical imaging system is shown and is generally identified by reference numeral 10. In this example, hybrid medical imaging system 10 comprises a nuclear imaging subsystem such as for example, a positron emission tomography (PET) subsystem 12 and a magnetic resonance imaging (MRI) subsystem 14. The PET subsystem 12 is intermediate the two ends of the MRI subsystem 14. The PET and MRI subsystems 12, 14 are coupled to a processing unit 16, such as for example a personal computer (PC) or other suitable processing device which executes programm code structure in suitable memory. The processing unit 16 in this embodiment comprises, for example, a processor, a system memory (volatile and/or non-volatile memory), other non-removable or removable memory (eg. a hard disk drive, RAM, ROM, EEPROM, CD-ROM, DVD, flash memory, etc.) and a system bus coupling the various components to the processor. The processing unit can include a network connection to access shared or remote drives, one or more networked computers, or other networked devices. The extent of an object, for example, a patient, animal or other subject, enclosed by the PET subsystem 12 can be imaged by both the PET subsystem 12 and the MRI subsystem 14 simultaneously. A patient bed 20 is moveable axially within the MRI subsystem 14 to position the subject lying on the bed at the desired location relative to the PET and MRI subsystems 12 and 14. Images acquired simultaneously by the PET subsystem 12 and MRI subsystem 14 are conveyed to the processing unit 16. The processing unit 16 in turn performs attenuation coefficient mapping techniques in order to yield corrected hybrid images.

Figure 2A:
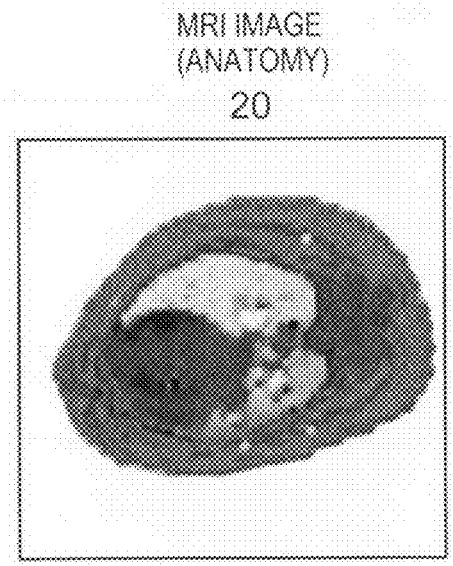
FIG. 2A shows an MRI image captured by the system of FIG. 1.

FIG. 2A shows an MRI image 20 captured by the MRI subsystem 14. As can be seen, MRI image 20 is an axial cross-section through the chest of a mammal, in this case a canine, revealing the mediastinum, lungs, and surrounding musculature and fat. As is known, the MRI subsystem 14 is capable of imaging the distribution of anatomy in the subject, which can include, for example, the distribution of muscle, fat, and nervous tissues as well as distortions to that anatomy resulting from disease or injury. The MRI subsystem 14 is said to image endogenous contrast since these tissue types can be distinguished by the MRI subsystem 14 due to differences in their physical properties.

Figure 2B:
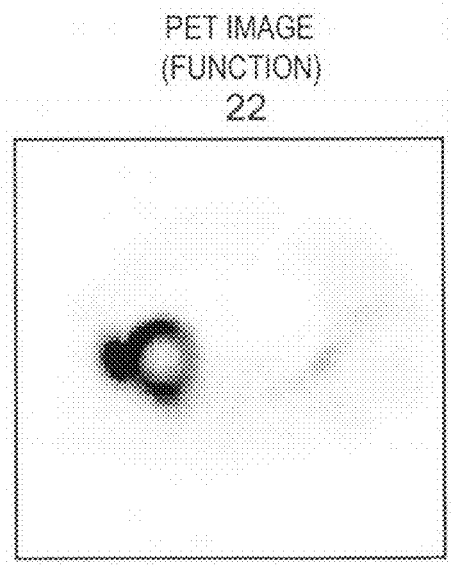
FIG. 2B shows a PET image captured by the system of FIG. 1 corresponding to the image shown in FIG. 2A.

Conversely, the PET subsystem 12 images the distribution of a radionuclide introduced into the subject. FIG. 2B shows a PET image 22 captured by the PET subsystem 12 corresponding to the MRI image 20 of FIG. 2A. As can be seen, the PET image 22 shows the distribution of a radiopharmaceutical that is designed to be taken up by myocardial tissue. The radionuclide is bound to a molecule, and the resulting construct termed a radiopharmaceutical. The radiopharmaceutical is designed to have a specific distribution in the subject, for example distributing according to cardiac blood flow or malignancy. However, radiopharmaceuticals often have some non-specific uptake, which can be used as spatial reference information in the absence of corresponding anatomical imaging. As mentioned above, FIGS. 2A and 2B correspond to each other, and are acquired simultaneously by the hybrid medical imaging system 10 as illustrated in FIG. 1.

Figure 3:
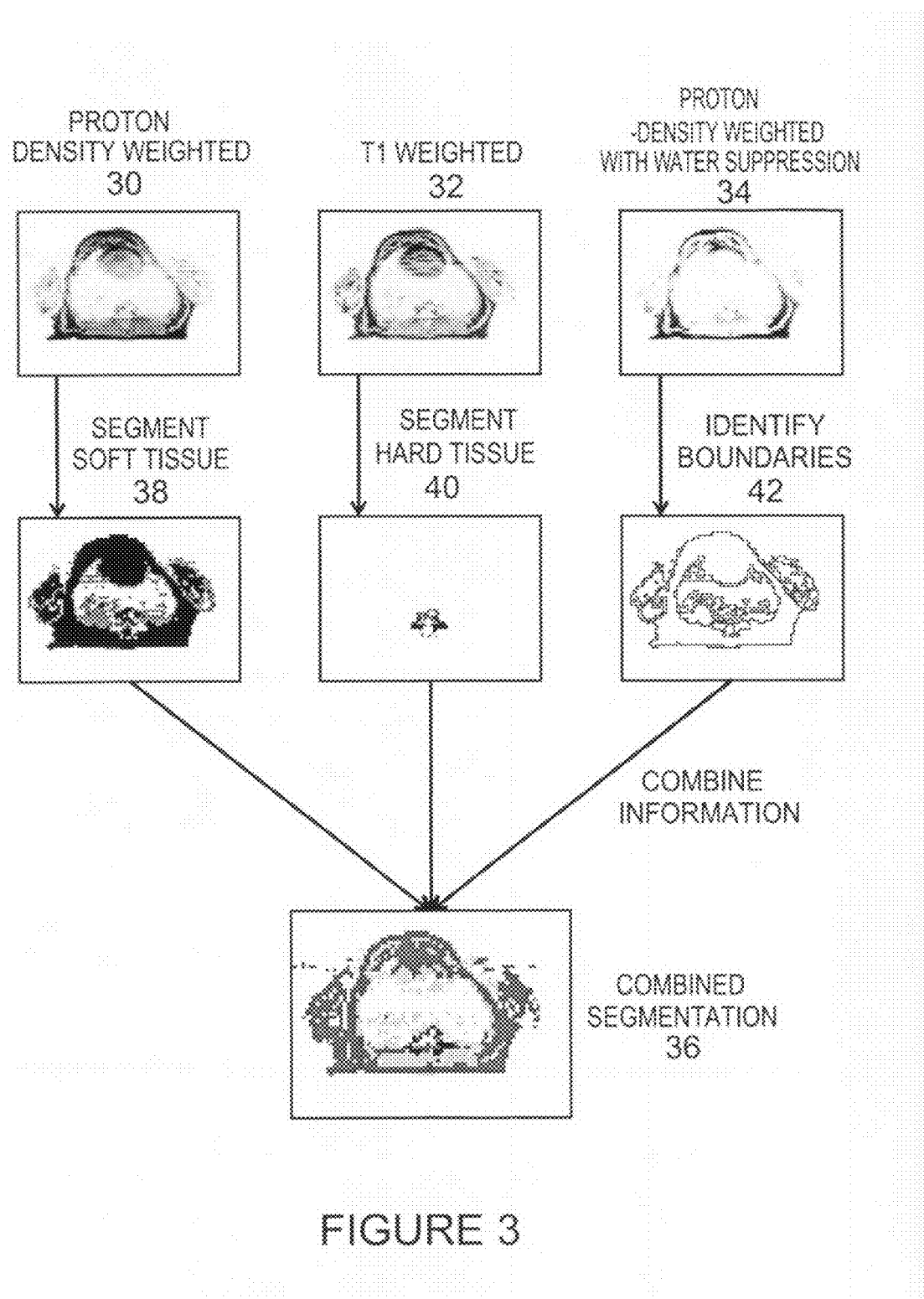
FIG. 3 shows MRI images based on different MRI parameters that are segmented and combined to yield a combined segmented MRI image.

FIG. 3 shows three (3) MRI images 30, 32 and 34 captured by the MRI subsystem 14 based on different MRI parameters and the processing of the MRI images carried out by the processing unit 16 in order to derive a combined segmented MRI image 36. In this example, the three (3) MRI images comprise a proton-density weighted MRI image 30, a T1 weighted (longitudinal relaxation weighted on T1w) MRI image 32 and a proton-density weighted with water suppression MRI image 34. During processing by the processing unit 16, the proton-density weighted MRI image 30 is segmented to identify soft tissue 38, the T1 weighted MRI image 32 is segmented to identify hard tissue 38, and the proton-density weighted with water suppression MRI image 34 is segmented to identify tissue boundries 40. There are a variety of methods for segmenting information from the MRI images. In this embodiment, the processing unit 16 employs the k-means algorithm to segment the MRI images 30 to 34. The information identified through segmentation of the MRI images 30 to 34 is then combined by the processing unit 16 to yield the combined segmented MRI image 36.

Figure 4:
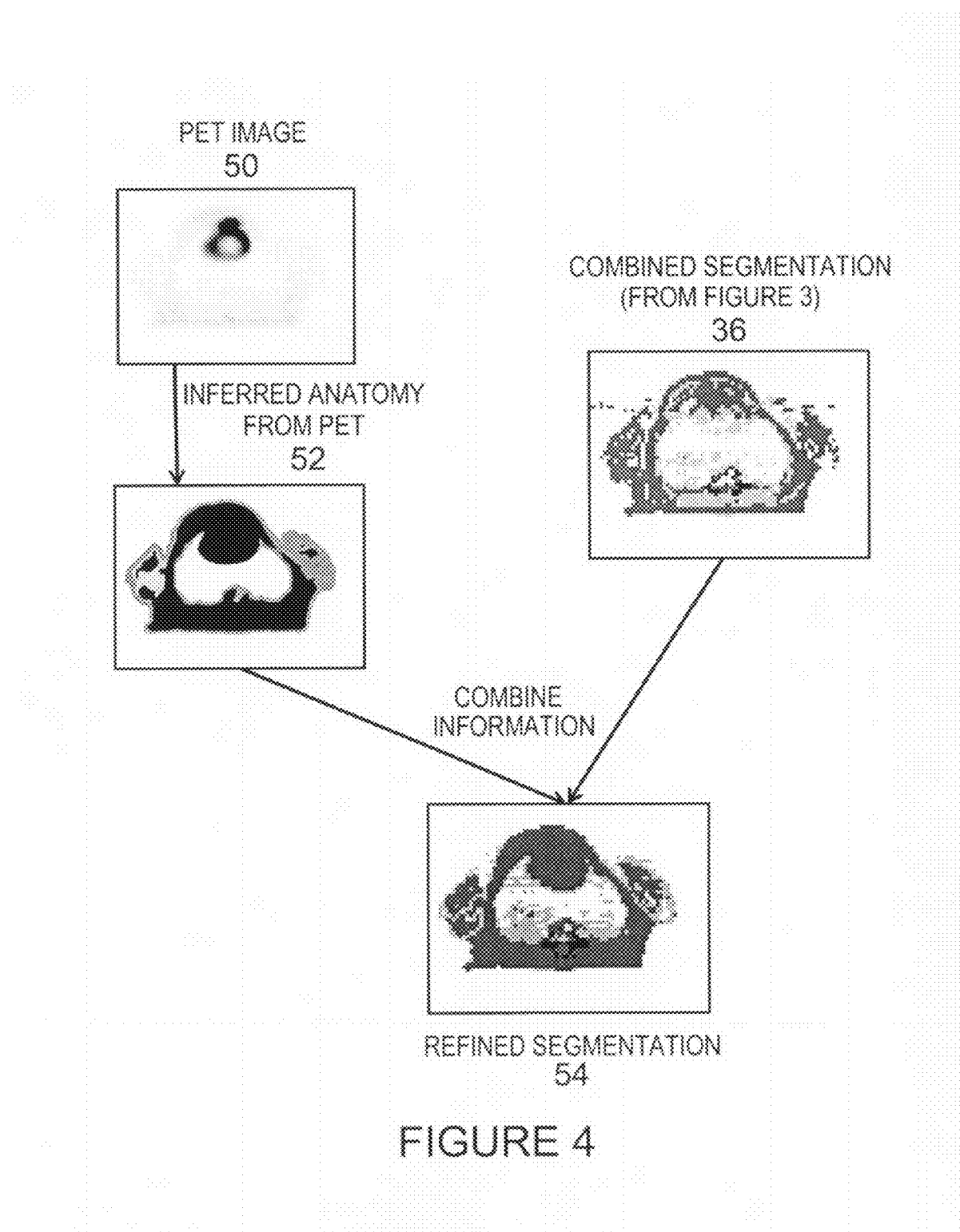
FIG. 4 shows a refined combined segmented MRI image derived from a PET image and the combined segmented MRI image of FIG. 3.

The quality of the combined segmented MRI image 36 is then refined by utilizing additional information that is derived from the PET subsystem 12, which acquires measurements of the distribution of radiopharmaceutical inside the subject. This refined segmentation assists in determining a more accurate estimate of the attenuation coefficient distribution. FIG. 4 shows a PET image 50 that is subjected to a preliminary tomographic reconstruction 52 by the processing unit 16 from which the contours, or support (i.e. anatomy), of the subject can be inferred via voxel-by-voxel thresholding of the reconstruction with some spatial smoothing. Other techniques for inferring anatomy, or identifying different tissue types inside the anatomy may however be employed such as for example, the techniques disclosed in support "Scatter and Attenuation Correction for Brain SPECT using Attenuation Distributions Inferred from a Head Atlas" authored by Stodilka et al. (J Nucl Med 41 1569-1578, 2000) and in U.S. Pat. No. 6,740,883 to Stodilka et al. After the PET image 50 has been processed to infer anatomy, the processing unit 16 combines the resultant information with the combined segmented MRI image 36 to yield a refined combined segmented MRI image 54. The quality of the refined combined segmentated MRI image 54 may be enhanced by providing information that cannot be discerned from MRI as easily, such as the location of bone or variations of attenuation coefficient in tissues that are visualized as having uniform MRI parameters, or tissues with the same attenuation coefficients that are visualized as having different MRI parameters.

Figure 5:
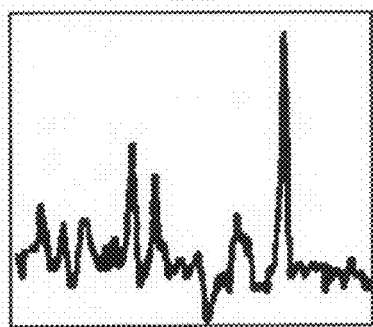
FIG. 5 shows an attenuation coefficient image derived from an attenuation coefficient lookup table and in situ MRI measurements and the refined combined segmented MRI image of FIG. 4.
Figure 5:
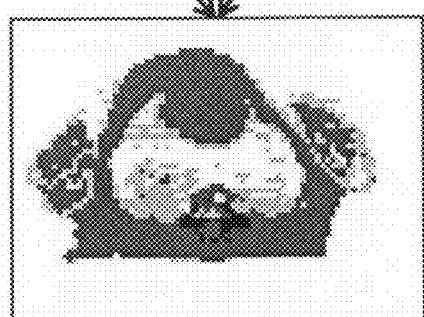

Once the refined combined segmented MRI image 54 has been generated, the processing unit 16 assigns attenuation coefficients to the various tissue types of the refined combined segmented MRI image to yield an attenuation coefficient image 60 as shown in FIG. 5. In this embodiment, the processing unit 16 derives attenuation coefficients for some tissue of the subject from a lookup table 62, and derives attenuation coefficients for other tissue via in situ MRI or Magnetic Resonance Spectroscopy (MRS) measurements of the subject 64. If desired, all of the attenuation coefficients may be derived from the lookup table 62 or all of the attenuation coefficients may be derived from the in situ measurements 64.

Alternatively, the MRI subsystem 14 can make measurements of the subject from which some or all of the attenuation coefficients 52 can be derived. For example, MRI techniques have been demonstrated for measuring bone density as described in "Biophysic evaluation of bone quality—application of Fourier transform infrared spectroscopy and phosphorus-31 solid-state nuclear magnetic resonance spectroscopy" authored by Takata et al. (J Med Invest 51 133-138, 2004) and "Magnetic Resonance Imaging Measurements of Bone Density and Cross-Sectional Geometry" authored by Hang et al. (Calcif Tissue Int 66 74-78, 2000). MRI techniques have also been demonstrated for measuring the attenuation coefficients for cortical and trabecular bone as described in "The Importance of Bone Attenuation in Brain SPECT Quantification" authored by Stodilka et al. (J Nucl Med 39 190-197, 1998). Information from these two sources can be combined with the refined combined segmented MRI image to yield the attenuation coefficient image.

Attenuation in PET occurs along the line connecting the origin of the gamma ray emissions and the detector element where those gamma rays are detected. Attenuation correction relies upon knowing the values of the line integrals on the attenuation coefficient images between those same two points (emission and detection) to determine the magnitude of attenuation correction that must be applied. In the case of PET imaging, this requirement is simplified in that it is sufficient to know only the line integrals between opposing detectors.

Figure 6:
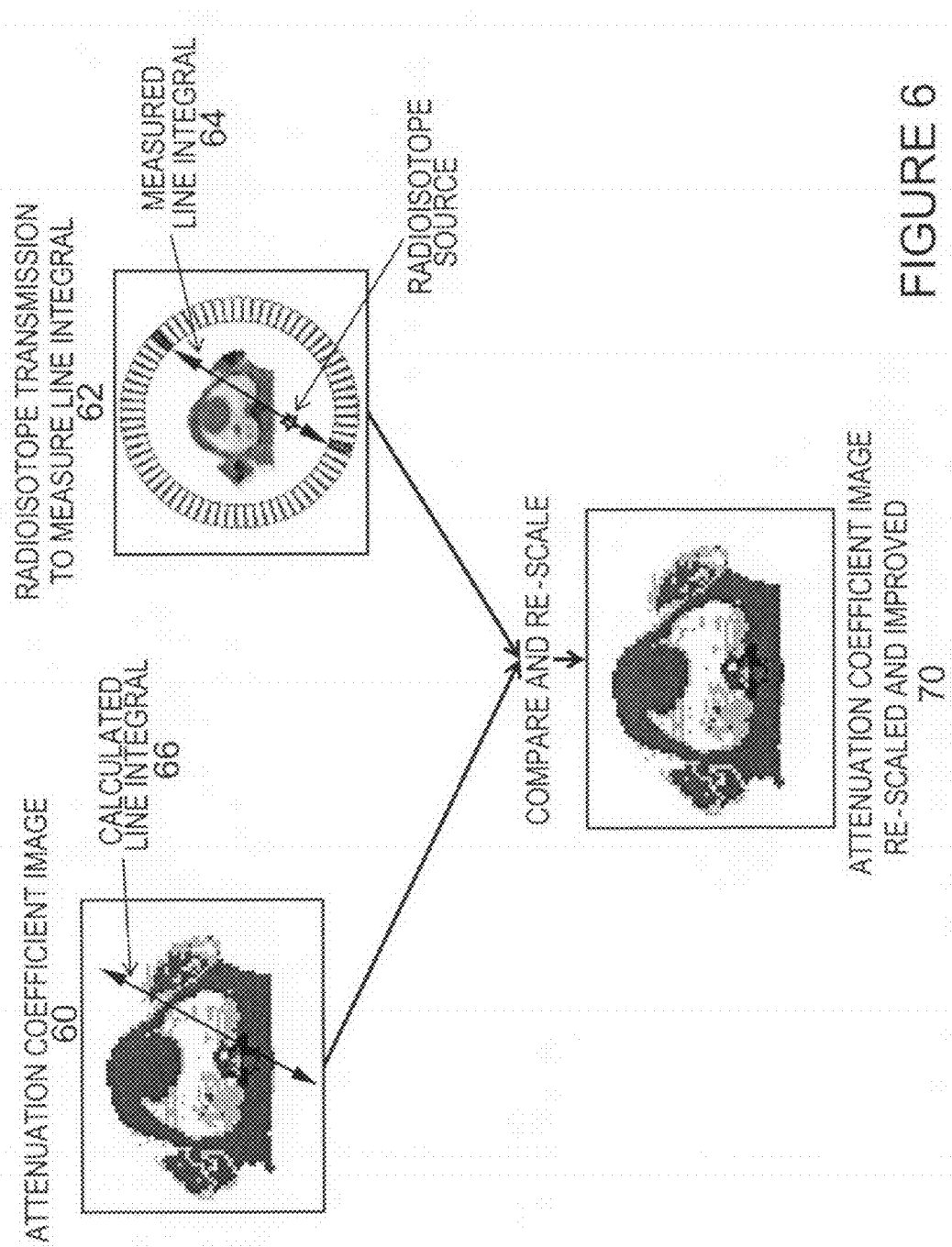
FIG. 6 shows a re-scaled attenuation coefficient image derived from measured and calculated line integrals through the attenuation coefficient image of FIG. 5.

FIG. 6 shows the attenuation coefficient image 60 and a line integral 64 measured with a radioisotope transmission system 62. The corresponding line integral 66 in the attenuation coefficient image 60 is calculated by the processing unit 16. Based on the differences between the measured line integral 64 and calculated line integral 66, the processing unit 16 recalculates and scales the attenuation coefficient image 70 such that the calculated line integral matches the measured line integral. With the attenuation coefficient image 70 re-scaled, the attenuation coefficient image is used by the processing unit to correct attenuation in the PET image.

Figure 7A:
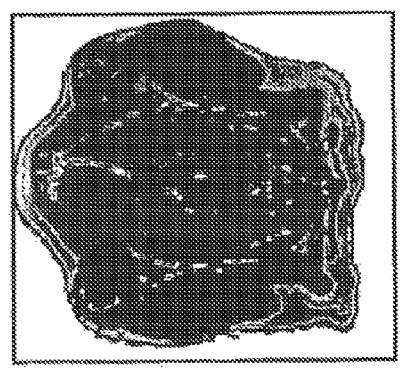
FIGS. 7A to 7F show sample MRI images based on different MRI parameters and attenuation coefficient images.
Figure 7B:
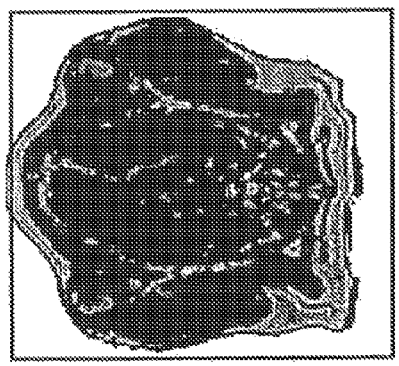
Figure 7C:
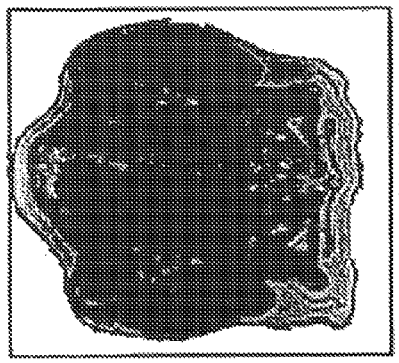
Figure 7D:
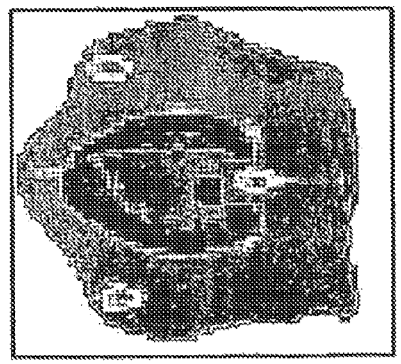
Figure 7E:
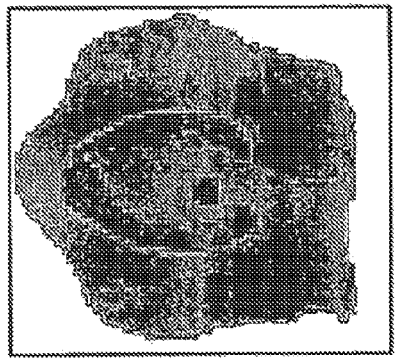
Figure 7F:
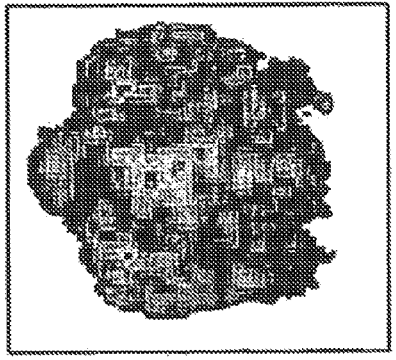

In one example, a healthy canine is anaesthetized, immobilized on a wooden platform, and injected with 18F-FDG. Sixty minutes later whole-body PET/CT images (Discovery LS, General Electric Healthcare, Waukesha, Wis.) are acquired. The canine, on the platform, is then moved to an MRI suite, and T1-weighted, T2-weighted, and proton density whole-body MRI images are acquired at 1.5T (Avanto, Siemens Medical Solutions, Erlangen, Germany). Subsequently, all MRI data are spatially registered to the CT data. In FIGS. 7A to 7F, resulting images are shown. In particular, FIGS. 7A to 7F show transaxial images through the canine at the thoracic level. FIG. 7A is a T1-weighted MRI image. FIG. 7B is a T2-weighted MRI image. FIG. 7C is a proton-density weighted MRI image. FIG. 7D is a X-ray CT image. FIG. 7E an MRI-derived attenuation map from 511-keV attenuation, and FIG. 7F is a PET image. In this example, multi-parameter MRI data is collected, and that data is mapped into attenuation coefficients suitable for use with PET. In PET/CT and SPECT/CT, the mapping from CT to attenuation coefficients is relatively straightforward since both are related to electron density—unlike multi-parameter MRI images (T1 weighted, T2 weighted, proton-density weighted).

CT data are converted to 511-keV attenuation coefficients, and registered to MRI. MRI data are segmented via k-means to classify tissue types for each MRI parameter (six (6) clusters per parameter), and known 511-keV attenuation coefficients are assigned to clusters to yield MRI-derived attenuation maps. Also, clusters from multiple MRI parameters are combined to yield a multi-parameter MRI-derived attenuation map. Single- and multi-parameter MRI-derived attenuation maps are evaluated by comparing radon transforms [Cho Z H, Jones J P, Singh M 1993 (line integrals) of those maps with radon transforms of the CT-derived attenuation maps as described in "Foundations of Medical Imaging" authored by Cho et al. (John Wiley & Sons Inc pg 73-74, 1993).].

Figure 8D:
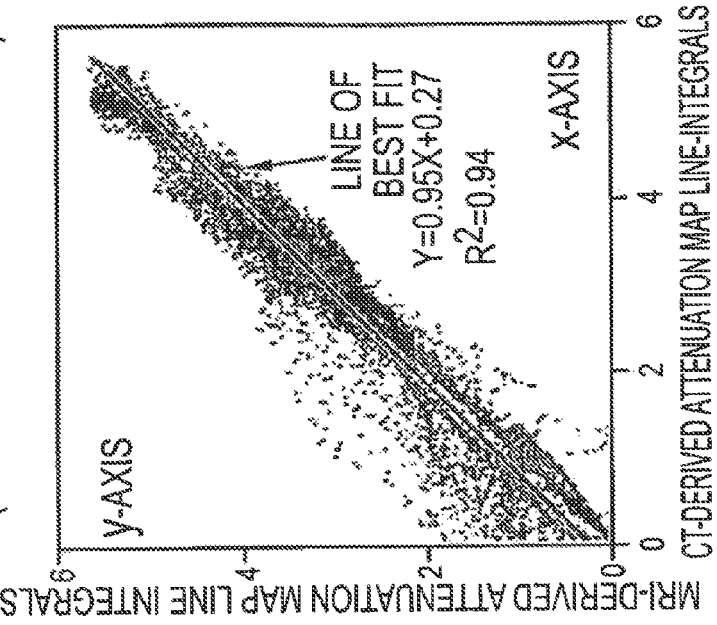
Figure 8D:
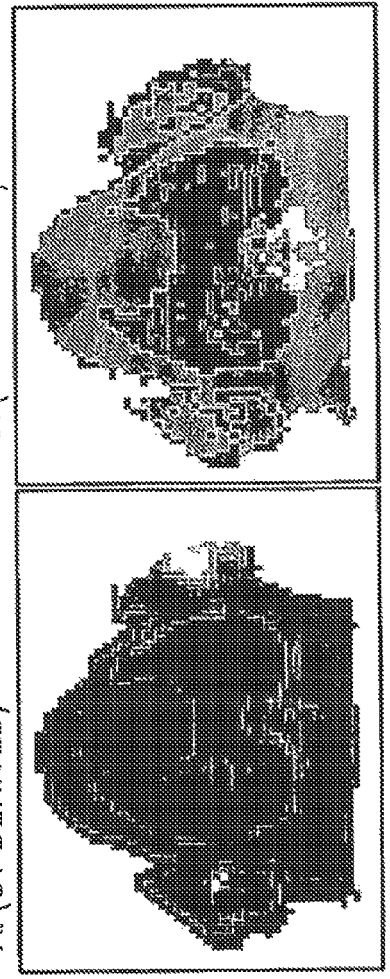

FIG. 8A shows a CT-derived attenuation map (axial slice at the thoracic level). FIG. 8B shows the corresponding MRI-derived attenuation map using T1, proton-density, and proton-density with water suppression MRI parameters. FIG. 8C shows the correlation of line integrals and line of best fit. FIG. 8D shows the results of line integral correlation, for thoracic and abdominal slices (not shown).

In this example, the proton-density MRI image contributed most to identifying soft tissue and lung and the proton-density with water suppression MRI image contributed most to edge and marrow detection. Multi-parameter segmentation outperformed single-parameter segmentation (see FIG. 8C and FIG. 8D). The best combination of MRI parameters in this example are T1 weighted, proton-density and proton-density with water suppression. Segmentation encounters challenges in regions near bone and cartilaginous structures, and performed best in abdominal axial slices with less bone.

The program code executed by the processing unit 16 may comprise program modules including but not limited to routines, programs, object components, data structures etc. and may be embodied as computer readable program code stored on a computer readable medium. The computer readable medium is any data storage device that can store data, which can thereafter be read by a computer system. Examples of computer readable medium include for example read-only memory, random-access memory, CD-ROMs, magnetic tape and optical data storage devices. The computer readable program code can also be distributed over a network including coupled computer systems so that the computer readable program code is stored and executed in a distributed fashion.

Those skilled in the art recognize that PET is only one modality capable of performing nuclear medicine imaging, and the T1 weighted, proton-density weighted and proton-density with water suppression MRI parameters are only some of the MRI parameters that can be measured with MRI. For example, single photon emission computed tomography may be employed. Also, T2 weighted (transverse relaxation weighted or T2w) MRI or other parameter based MRI images can be used. As will be appreciated, different MRI parameters provide different contrasts in the subject being imaged. Imaging with certain MRI parameters may improve contrasts in tissues with relatively large amounts of water. Also, data acquisition in the MRI subsystem 14 can be modified to suppress contrast from other materials besides water as in the proton-density with water suppression MRI images.

The MRI parameters that are selected for imaging are chosen to suit the imaging environment and permit suitable distribution of attenuation coefficients. As will be appreciated, certain MRI parameters yield superior segmentation results for certain tissues although segmentation can depend on the segmentation algorithm employed and/or the MRI image acquisition sequence.

Although the hybrid medical imaging system 10 is described as acquiring PET and MRI images simultaneously, those of skill in the art will appreciate that the PET and MRI images may be acquired sequentially or the PET and MRI images may be acquired alternatively.

Although preferred embodiments have been described with reference to the drawings, those of skill in the art will appreciate that variations and modifications may be made without departing from the spirit and scope thereof as defined by the appended claims.

What is claimed is:

1. An integrated hybrid medical imaging system comprising:
    a nuclear medicine imaging subsystem configured to capture an image of a target region of a subject;
    a magnetic resonance imaging (MRI) subsystem configured to capture a plurality of MRI images of said target region, each MRI image being based on a different MRI parameter that highlights a specific tissue type and being captured simultaneously with the image captured by said nuclear medicine imaging subsystem, the different MRI parameters being selected to identify a plurality of different tissue types within said target region; and
    a processor configured to:
    process the MRI images to measure the different MRI parameters,
    estimate attenuation of the different tissue types with said target region from the measured MRI parameters,
    generate a non-uniform attenuation map of said target region, wherein the non-uniform attenuation map is generated from a combination of individual captures, wherein a first capture of the individual captures is weighted by an MRI parameter including one of longitudinal relaxation weighted, transverse relaxation weighted, proton-density weighted, or proton-density weighted with water suppression, wherein a second capture of the individual captures is weighted by a different MRI parameter than the first capture, and
    use the non-uniform attenuation map to correct the image captured by said nuclear medicine imaging subsystem.

2. The system of claim 1 wherein said different MRI parameters are selected at least to identify soft tissue, hard tissue and/or tissue boundaries within said target region.

3. The system of claim 1 wherein said nuclear medicine imaging subsystem comprises one of a positron emission tomography and a single photon emission computed tomography imaging subsystem.

4. The system of claim 1 wherein the processor is further configured to use measurements from the nuclear medicine imaging subsystem to assist in identifying soft tissue, hard tissue and/or tissue boundaries within said target region to facilitate said generating of the non-uniform attenuation map.

5. The system of claim 1 wherein said processor is configured to segment each of said MRI images to identify information of interest in each MRI image and to combine the segmented MRI images to yield a combined segmented MRI image, said processor configured to assign attenuation values of said non-uniform attenuation map to the combined segmented MRI image to yield an attenuation coefficient image and to use the attenuation coefficient image to correct the image captured by said nuclear medicine imaging subsystem.

6. The system of claim 5 wherein said processor is configured to refine the combined segmented MRI image prior to assigning the attenuation values of said non-uniform attenuation map to the combined segmented MRI image.

7. The system of claim 6 wherein said processor is configured to use the image captured by the nuclear medicine imaging subsystem to refine the combined segmented MRI image.

8. The system of claim 5 wherein said processor is configured to assign attenuation values of said non-uniform attenuation map to the combined segmented MIR image using at least one of a lookup table and in situ imaging measurements.

9. The system of claim 8 wherein said processor is configured to assign attenuation values of said non-uniform attenuation map to the combined segmented MRI image using both the lookup table and in situ imaging measurements.

10. The system of claim 5 wherein said processor is configured to rescale the attenuation coefficient image prior to using the attenuation coefficient image to correct the image captured by said nuclear medicine imaging subsystem.

11. The system of claim 1 wherein said processor is configured to infer anatomy from the image captured by the nuclear medicine imaging subsystem to facilitate said generating of the non-uniform attenuation map.

12. The system of claim 11 wherein said processor is configured to rescale the attenuation coefficient image prior to using the attenuation coefficient image to correct the image captured by said nuclear medicine imaging subsystem.

13. The system of claim 11 wherein said processor is configured to assign attenuation values of said non-uniform attenuation map to the combined segmented MRI image using at least one of a lookup table and in situ imaging measurements.

14. The system of claim 13 wherein said processor is configured to assign attenuation values of said non-uniform attenuation map to the combined segmented MRI image using both the lookup table and in situ imaging measurements.

15. The system of claim 13 wherein said processor is configured to rescale the attenuation coefficient image prior to using the attenuation coefficient image to correct the image captured by said nuclear medicine imaging subsystem.

16. A method for hybrid medical imaging comprising:
capturing a nuclear medicine image of a target region of a subject based on a radioactive contrast agent in said subject;
capturing a plurality of MRI images of said target region, each MRI image being based on a different MRI parameter that highlights a specific tissue type and being captured simultaneously with said nuclear medicine image, the different MRI parameters being selected to identify a plurality of different tissue types within said target region;
processing, using a processor, the MRI images to measure the different MRI parameters; and
estimating, using the processor, attenuation of the different tissue types within said target region from the measured MRI parameters to generate a non-uniform attenuation map of said target region, wherein the non-uniform attenuation map is generated from a combination of individual captures, wherein a first capture of the individual captures is weighted by an MRI parameter including one of longitudinal relaxation weighted, transverse relaxation weighted, proton-density weighted, or proton-density weighted with water suppression, wherein a second capture of the individual captures is weighted by a different MRI parameter than the first capture; and
correcting, using the processor, degradations in said nuclear medicine image using the non-uniform attenuation map.

17. A non-transitory computer readable medium embodying computer program code for causing a processor of a hybrid medicine imaging system to:
capture a nuclear medicine image of a target region of a subject based on a radioactive contract agent in said subject;
capture a plurality of MRI images of said target region, each MRI image being based on a different MRI parameter that highlights a specific tissue type and being captured simultaneously with said nuclear medicine image, the different MRI parameters being selected to identify a plurality of different tissue types;
process the MRI images to measure the different MRI parameters, estimate attenuation of the different tissue types within said target region from the measured MRI parameters and generate a non-uniform attenuation map of said target region, wherein the non-uniform attenuation map is generated from a combination of individual captures, wherein a first capture of the individual captures is weighted by an MRI parameter including one of longitudinal relaxation weighted, transverse relaxation weighted, proton-density weighted, or proton-density weighted with water suppression, wherein a second capture of the individual captures is weighted by a different MRI parameter than the first capture; and
correct degradations in said nuclear medicine image using the non-uniform attenuation map.

18. A method for hybrid medical imaging comprising:
measuring a plurality of intrinsic MRI parameters of a target region of a subject based on a plurality of MRI images of the target region captured simultaneously with a nuclear medicine image of said target region, each MRI image being based on a different intrinsic MRI property that highlights a specific tissue type, the intrinsic MRI parameters being selected to identify a plurality of different tissue types within said target region;
processing, by a processor, the measured intrinsic MRI parameters to estimate attenuation of the different tissue types within the target region from the measured intrinsic MRI parameters and to generate a non-uniform attenuation map of said target region, wherein the non-uniform attenuation map is generated from a combination of individual captures, wherein a first capture of the individual captures is weighted by an MRI parameter including one of longitudinal relaxation weighted, transverse relaxation weighted, proton-density weighted, or proton-density weighted with water suppression, wherein a second capture of the individual captures is weighted by a different MRI parameter than the first capture; and
correcting degradations in a nuclear medicine image of the target region using the non-uniform attenuation map.

19. The method of claim 18 wherein said processing further comprises:
inferring anatomy from the nuclear medicine image to facilitate said generating of the non-uniform attenuation map.

20. The method of claim 18 wherein said attenuation values are assigned using at least one of a lookup table and in situ imaging measurements.

21. The method of claim 18 wherein said attenuation coefficient image is restructured prior to said using.

22. The method of claim 18 wherein said plurality of intrinsic MRI parameters are selected at least to identify soft tissue, hard tissue and/or tissue boundaries within said target region.

23. The method of claim 22 wherein said processing comprising:
   segmenting each of said MRI images to identify information of interest in each MRI image;
   combining the segmented MRI images to yield a combined segmented MRI image; and
   assigning attenuation values of said non-uniform attenuation map to the combined segmented MRI image to yield an attenuation coefficient image, and
   wherein said correcting comprises using the attenuation coefficient image to correct the nuclear medicine image.

24. The method of claim 23 wherein said processing further comprises refining the combined segmented MRI image prior to assigning the attenuation values.

25. The method of claim 24 wherein said refining comprises using the nuclear medicine image to refine the combined segmented MRI image.

\* \* \* \* \*